United States Patent
Asada et al.

(10) Patent No.: US 9,126,088 B2
(45) Date of Patent: Sep. 8, 2015

(54) BODY MOVEMENT AMOUNT MEASURING APPARATUS

(75) Inventors: Yuji Asada, Muko (JP); Naoki Takeishi, Muko (JP); Motofumi Nakanishi, Muko (JP); Yusuke Kawabe, Muko (JP); Mamoru Katano, Muko (JP); Yoko Shimose, Muko (JP); Tamaki Ito, Muko (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 14/238,259

(22) PCT Filed: Jun. 6, 2012

(86) PCT No.: PCT/JP2012/064508
§ 371 (c)(1),
(2), (4) Date: Feb. 11, 2014

(87) PCT Pub. No.: WO2013/024619
PCT Pub. Date: Feb. 21, 2013

(65) Prior Publication Data
US 2014/0200857 A1 Jul. 17, 2014

(30) Foreign Application Priority Data
Aug. 12, 2011 (JP) .................................. 2011-176828

(51) Int. Cl.
*G04B 47/06* (2006.01)
*A63B 69/00* (2006.01)
(Continued)

(52) U.S. Cl.
CPC ........... *A63B 69/0028* (2013.01); *A61B 5/1118* (2013.01); *A61B 5/4866* (2013.01); *G01C 22/006* (2013.01); *A61B 2562/0219* (2013.01)

(58) Field of Classification Search
CPC . G04B 47/063; G01C 22/006; A61B 5/02438
USPC .............. 702/141, 149, 150, 160; 73/49, 510; 235/105
See application file for complete search history.

(56) References Cited

U.S. PATENT DOCUMENTS

| 5,788,655 A | 8/1998 | Yoshimura et al. |
| 7,959,539 B2 * | 6/2011 | Takeishi et al. .................... 482/8 |

(Continued)

FOREIGN PATENT DOCUMENTS

| JP | 63-135473 U | 9/1988 |
| JP | 08-308820 A | 11/1996 |

(Continued)

OTHER PUBLICATIONS

Official Communication issued in International Patent Application No. PCT/JP2012/064508, mailed on Jul. 17, 2012.

*Primary Examiner* — Sujoy Kundu
*Assistant Examiner* — Ricky Ngon
(74) *Attorney, Agent, or Firm* — Keating & Bennett, LLP

(57) ABSTRACT

An activity meter includes a body movement detecting unit, a display unit, a target activity amount acquiring unit, an accumulated activity amount calculation unit, an excess activity amount calculation unit, a converted value calculation unit that calculates a converted value representing an excess amount of activity by dividing burned calories corresponding to the excess amount of activity by a unit calorie count, where a standard calorie count of a predetermined food is the unit calorie count, and a display operation control unit that controls a display operation of the display unit such that the display unit displays a measurement result using the converted value.

12 Claims, 11 Drawing Sheets

(51) Int. Cl.
*A61B 5/11* (2006.01)
*A61B 5/00* (2006.01)
*G01C 22/00* (2006.01)

(56) References Cited

U.S. PATENT DOCUMENTS

| | | | |
|---|---|---|---|
| 8,036,850 B2* | 10/2011 | Kulach et al. | 702/141 |
| 2010/0057397 A1* | 3/2010 | Takeishi et al. | 702/160 |
| 2011/0112861 A1* | 5/2011 | Hama | 705/2 |
| 2011/0197157 A1* | 8/2011 | Hoffman et al. | 715/772 |
| 2012/0042726 A1* | 2/2012 | Jeon et al. | 73/490 |

FOREIGN PATENT DOCUMENTS

| | | |
|---|---|---|
| JP | 11-178967 A | 7/1999 |
| JP | 2001-67083 A | 3/2001 |
| JP | 2008-86480 A | 4/2008 |
| JP | 2008-117174 A | 5/2008 |
| JP | 2010-193318 A | 9/2010 |

* cited by examiner

BODY MOVEMENT AMOUNT MEASURING APPARATUS

BACKGROUND OF THE INVENTION

1. Field of the Invention

The present invention relates to a body movement amount measuring apparatus that measures an amount of body movement by detecting body movement, and more particularly, relates to an activity meter, a pedometer, or the like which serves as a body movement amount measuring apparatus that is configured to be able to identify an excess amount of body movement (excluding cases where the excess amount of body movement is a deficient amount of body movement that is represented by a negative value, the same shall apply hereinafter).

2. Description of the Related Art

Body movement amount measuring apparatuses are apparatuses that measure the amount of body movement (i.e., vibrations associated with movement of the body) of a user by detecting body movement of the user. Conventionally, the use of pedometers that can measure the number of steps, which is the amount of body movement, based on the detected body movement and measure the walking distance, the calories burned by walking, and the like that are calculated based on the number of steps has become widespread. Also, in recent years, the use of activity meters that can measure, for example, the total calories burned by activities, including walking, of a day by acquiring the amount of not only walking but also other activities as the amount of activity, which is the amount of body movement, based on the detected body movement has been widespread.

Pedometers and activity meters are often used as apparatuses for supporting the user in working on a diet. Thus, pedometers and activity meters are known that have a function of allowing the user to set a target value, such as the number of steps the user should walk in one day, the amount of activity the user should perform in one day, or the like, and informing the user of whether or not the target value is reached or the difference from the target value in order to assure the success of the diet.

For example, JP 63-135473U discloses a pedometer that is configured to inform the user when a preset target number of steps is reached using a display unit and a buzzer.

Moreover, JP 2008-117174A discloses a pedometer that is configured to compare an accumulated number of steps measured in a measurement period with a preset target number of steps and inform the user of an excess number of steps by graphical representation.

Furthermore, JP 11-178967A discloses an activity meter that is configured to compare an accumulated amount of activity measured in a measurement period with a preset target amount of activity and inform the user of an excess amount of activity by displaying a figure that is suggestive of a daily event that is considered to be likely to happen to the user.

Note that in addition to the above described apparatuses, a body movement amount measuring apparatus is known that is configured to compare an accumulated amount of body movement measured in a measurement period with a preset target amount of body movement and inform the user of an excess amount of body movement by numerical representation.

However, in cases where body movement amount measuring apparatuses are considered as apparatuses for supporting a diet as described above, whichever of the foregoing methods of display is employed, it is difficult for the user to intuitively and specifically understand how hard the user is working on the diet.

That is to say, in cases where the excess amount of body movement is displayed by numerical representation, graphical representation, or using a figure that is suggestive of a daily event that is considered to be likely to happen to the user, even though the relationship between the target amount of body movement and the accumulated amount of body movement (i.e., the relationship between the target value and an actually achieved value) can be understood as an achievement rate or level, it is difficult to intuitively and specifically understand to what extent the effect of the diet is achieved or to what extent the effect of the diet is deficient.

SUMMARY OF THE INVENTION

Therefore, in view of the above-described problems, preferred embodiments of the present invention provide a body movement amount measuring apparatus that enables the user to more intuitively and specifically understand how hard the user is working on a diet.

Generally, it is said that the key to success in a diet is to sufficiently suppress calorie intake while avoiding excessive suppression and to simultaneously increase burned calories. Thus, paying attention to the fact that a user who is on a diet is interested in not only increasing the burned calories but also suppressing the calorie intake, the inventor of the present invention conceived that it is possible to enable the user to more intuitively and specifically understand how hard he/she is working on a diet by displaying the excess amount of body movement in relation to calorie intake, and thus the inventor developed the preferred embodiments of the present invention.

That is, a body movement amount measuring apparatus according to a preferred embodiment of the present invention is a body movement amount measuring apparatus that measures an amount of body movement by detecting body movement, the apparatus including a display unit that displays a measurement result, a target body movement amount acquiring unit that acquires a target amount of body movement in a predetermined time period, a body movement detecting unit that detects body movement, an accumulated body movement amount calculation unit that calculates an accumulated amount of body movement from a beginning of the predetermined time period based on a detection result of the body movement detecting unit, an excess body movement amount calculation unit that calculates an excess amount of body movement by which the accumulated amount of body movement exceeds the target amount of body movement by subtracting the target amount of body movement from the accumulated amount of body movement, a converted value calculation unit that calculates a converted value representing the excess amount of body movement by dividing burned calories corresponding to the excess amount of body movement by a unit calorie count, where a standard calorie count of a predetermined food is the unit calorie count, and a display operation control unit that is programmed to control a display operation of the display unit such that the display unit displays a measurement result using the converted value.

It is preferable that the display operation control unit causes the display unit to display as many icons of a design that shows the food as a number corresponding to the converted value.

It is preferable that the display operation control unit controls the display operation of the display unit such that the display unit displays the accumulated amount of body movement as the measurement result.

It is preferable that the display operation control unit enables the display unit to display the accumulated amount of body movement as the measurement result before the predetermined time period elapses, and enables the display unit to display the measurement result using the converted value as the measurement result after the predetermined time period elapses.

It is preferable that the body movement amount measuring apparatus according to a preferred embodiment of the present invention further includes a display operation unit that accepts an instruction to cause the display unit to display the measurement result using the converted value. In that case, it is preferable that the display operation control unit causes the display unit to display the measurement result using the converted value only after the predetermined time period elapses and at a point in time when an initial operation of the display operation unit is accepted.

It is preferable that the body movement amount measuring apparatus according to a preferred embodiment of the present invention further includes a display starting time acquiring unit that acquires a starting time from which the display unit should be enabled to display the measurement result using the converted value after the predetermined time period elapses. In that case, it is preferable that the display operation control unit enables the display unit to display the measurement result using the converted value at a point in time when the starting time is reached.

It is preferable that the body movement amount measuring apparatus according to a preferred embodiment of the present invention further includes a non-display period acquiring unit that acquires a non-display period for which the display unit should not display the measurement result using the converted value after the predetermined time period elapses. In that case, it is preferable that the display operation control unit causes the display unit to be unable to display the measurement result using the converted value during the non-display period.

It is preferable that the display operation control unit is programmed to control the display operation of the display unit such that, at a point in time when the accumulated amount of body movement reaches the target amount of body movement, the display unit displays a mark of a design that is suggestive of the fact that the accumulated amount of body movement has reached the target amount of body movement.

It is preferable that the predetermined time period is taken as a unit time period, and a time period for which measurement of the amount of body movement should be continuously performed is covered by repeating the unit time period.

It is preferable that the body movement amount measuring apparatus according to a preferred embodiment of the present invention further includes a storage unit that stores the measurement result with respect to each unit time period. In that case, it is preferable that the display operation control unit is programmed to control the display operation of the display unit such that the measurement result with respect to each unit time period stored in the storage unit can be read out and displayed on the display unit for each unit time period.

It is preferable that when causing the display unit to display the measurement result with respect to each unit time period, the display operation control unit is programmed to cause the display unit to simultaneously display an accumulated amount of body movement in a selected unit time period and a measurement result using a converted value that represents an excess amount of body movement in a unit time period that is immediately before the selected unit time period.

It is preferable that the body movement detecting unit and the display unit are provided in a single portable terminal.

It is preferable that the body movement amount measuring apparatus according to a preferred embodiment of the present invention further includes a portable first terminal in which the body movement detecting unit is provided and a second terminal that is communicable with the first terminal via a communication device. In that case, it is preferable that the converted value is stored in a storage unit provided in the second terminal in a cumulative manner.

It is preferable that the amount of body movement is an amount of activity or a number of steps.

According to various preferred embodiments of the present invention, it is possible to provide a body movement amount measuring apparatus that enables a user to more intuitively and specifically understand how hard he/she is working on a diet.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described in detail with reference to the drawings. Note that in all of Preferred Embodiments 1 to 4 below, a case where the present invention is applied to an activity meter, which is a body movement amount measuring apparatus, will be described as an example. In Preferred Embodiments 1 to 4

Preferred Embodiment 1

Figure 1:
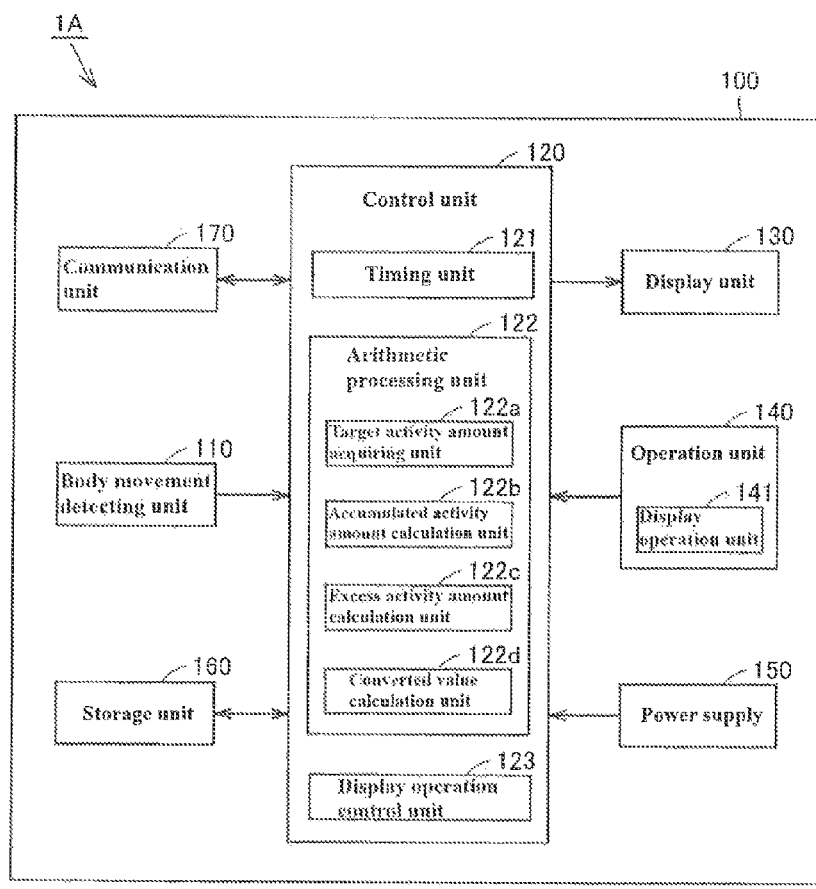
FIG. 1 is a diagram illustrating the configuration of functional blocks of an activity meter according to Preferred Embodiment 1 of the present invention.

FIG. 1 is a diagram illustrating the configuration of functional blocks of an activity meter according to Preferred Embodiment 1 of the present invention. First, referring to FIG. 1, the configuration of functional blocks of an activity meter 1A according to this preferred embodiment will be described.

The activity meter 1A of this preferred embodiment is configured to calculate an accumulated amount of activity with respect to each unit time period, where 24 hours from 0:00 to 0:00 the next day is taken as a unit time period of a measurement period (i.e., a unit time period corresponds to one day), while covering a period (e.g., 4 weeks) for which measurement of the amount of activity, which is the amount of body movement, should be continuously performed by repeating the unit time period, to calculate an excess amount of activity based on a previously acquired target amount of activity and the calculated accumulated amount of activity, to further calculate a converted value indicating the excess amount of activity based on the calculated excess amount of activity by associating burned calories corresponding to the excess amount of activity with a standard calorie count of a predetermined food, and to display a measurement result using the calculated converted value, thus being capable of informing a user of the result with respect to each unit time period in terms of how hard the user is working on a diet.

As illustrated in FIG. 1, the activity meter 1A of this preferred embodiment is preferably configured by a single portable terminal 100 in which various functional blocks are provided. The size of this terminal 100 is preferably reduced to such a size that fits in the palm so that the user can perform daily movements while wearing the terminal 100. The activity meter 1A detects a body movement of the user, thus measuring the amount of activity based on the detected body movement. The aforementioned daily movements include activities such as walking, housework, desk work, jogging, and the like.

The activity meter 1A mainly includes a body movement detecting unit 110, a control unit 120, a display unit 130, an operation unit 140, a power supply 150, a storage unit 160, and a communication unit 170 serving as a communication device.

The body movement detecting unit 110 is a unit that is arranged and configured to detect a body movement of the user and outputs an electric signal corresponding to the detected body movement to the control unit 120. Preferably, the body movement detecting unit 110 is configured by an acceleration sensor. Here, the acceleration sensor that is used may be a one-dimensional acceleration sensor that detects acceleration in one direction, may be a two-dimensional acceleration sensor that detects acceleration in two orthogonal directions, or may be a three-dimensional acceleration sensor that detects acceleration in three directions that are orthogonal to one another. However, in order to measure the amount of activity with higher accuracy, it is preferable to use a three-dimensional acceleration sensor, which provides a larger amount of information regarding the detected body movement, as the body movement detecting unit 110.

The control unit 120 is a unit that is configured and programmed to perform overall control of the activity meter 1A and is configured by, for example, a CPU (Central Processing Unit). The control unit 120, for example, accepts input of an instruction from the user through the operation unit 140, accepts an input from the body movement detecting unit 110 and calculates the amount of activity as a measurement result, outputs the calculated measurement result to the display unit 130, the storage unit 160, and the communication unit 170, reads out and executes a program that is stored in the storage unit 160 in advance, and so on.

The control unit 120 includes a timing unit 121, an arithmetic processing unit 122, and a display operation control unit 123. The timing unit 121 is a unit that is configured and programmed to measure time and is configured by, for example, an internal clock of the control unit 120. The arithmetic processing unit 122 is a unit that is configured and programmed to perform various types of arithmetic operations and mainly includes a target activity amount acquiring unit 122a, an accumulated activity amount calculation unit 122b, an excess activity amount calculation unit 122c, and a converted value calculation unit 122d. The display operation control unit 123 is a unit that is configured and programmed to control a display operation of the display unit 130.

Here, the display operation control unit 123 is configured to control the display operation of the display unit 130 such that the display unit 130 executes various types of display operations, which will be described later, and controls the display operation of the display unit 130 such that, when the user performs a predetermined operation, measurement results stored in the storage unit 160 for each day, which is a unit time period, are read out for each unit time period and displayed on the display unit 130.

The target activity amount acquiring unit 122a is a unit that acquires a target amount of activity by performing predetermined arithmetic processing based on information on the user, which will be described later. The accumulated activity amount calculation unit 122b is a unit that calculates an accumulated amount of activity from the beginning of the above-described unit time period based on the detection result of the body movement detecting unit 110.

The excess activity amount calculation unit 122c is a unit that calculates an excess amount of activity by subtracting the target amount of activity, which is acquired by the target activity amount acquiring unit 122a, from the accumulated amount of activity, which is calculated by the accumulated activity amount calculation unit 122b. The converted value calculation unit 122d is a unit that calculates a converted value indicating the excess amount of activity by dividing burned calories corresponding to the excess amount of activity, which is calculated by the excess activity amount calculation unit 122c, by a unit calorie count, where a standard calorie count of a predetermined food is the unit calorie count.

Note that the control unit 120 outputs the calculated accumulated amount of activity and excess amount of activity and the above-described converted value to the storage unit 160 when necessary. The storage unit 160 stores the information input from the control unit 120 for a required period of time.

The display unit 130 is a unit that displays a measurement result and the like, and the operation thereof is controlled by a control signal output from the display operation control unit 123, which is included in the control unit 120. The display unit 130 is configured by, for example, a display panel such as an LCD (Liquid Crystal Display) and is provided on the surface of a housing constituting a shell of the terminal 100.

The operation unit 140 is a unit that accepts instructions from the user. When operated by the user, the operation unit 140 outputs this operation to the control unit 120. The operation unit 140 is configured by, for example, push buttons and is provided on the surface of the housing that constitutes the shell of the terminal 100. The operation unit 140 includes a button to turn on and off the power supply, a button to input information on the user, a button to switch the state of display of the display unit 130, and the like. In addition, the operation unit 140 includes the display operation unit 141 that causes the display unit 130 to perform a specific display operation (details of this will be described later).

Now, the above-described information on the user preferably includes the gender, age, weight, and height of the user, a target weight reduction value that the user desires to lose in going on a diet, and the like. The control unit 120 that has accepted input of the above-described information through the operation unit 140 calculates the target amount of activity by performing predetermined arithmetic processing in the target activity amount acquiring unit 122a and outputs a calculated target amount to the storage unit 160. Note that although a description of a specific method for calculating the target amount of activity is not given here, a known calculation method can be used, for example. The storage unit 160 stores the target amount of activity input from the control unit 120 during a period for which the above-described measurement of the amount of activity should be continuously performed.

The power supply 150 supplies electric power to the control unit 120 and supplies electric power to the control unit 120 in accordance with a user operation through the operation unit 140. The power supply 150 is configured by, for example, a dry cell such as a button cell, a rechargeable battery, or the like.

The storage unit 160 stores programs that cause the control unit 120 and the like to execute various types of arithmetic processing and temporarily stores the above-described target amount of activity for each unit time period, measurement results, and the like, and is configured by, for example, a ROM (Read-Only Memory) and a RAM (Random-Access Memory). In particular, the use of an EEPROM (Electrically Erasable Programmable Read-Only Memory), which is a type of nonvolatile memory, as the storage unit enables various types of data to be retained even in the state in which the power supply is turned off. The storage unit 160 exchanges electric signals mainly with the control unit 120. Note that an external memory such as an SD memory card may also be used as the storage unit 160.

The communication unit 170 performs communication with an external terminal and is configured by, for example, a communication interface including such as a USB (Universal Serial Bus) to connect to an external terminal through wire or FeliCa (registered trademark), Bluetooth (registered trademark), or the like as NFC (Near Field Communication) to perform wireless communication with an external terminal. The communication unit 170 exchanges electric signals mainly with the control unit 120. Providing the activity meter 1A with this communication unit 170 makes it possible to realize communication between the activity meter 1A and an information processing apparatus represented by a PC (Personal Computer), a smartphone, a PDA (Personal Digital Assistant), and the like.

Figure 2:
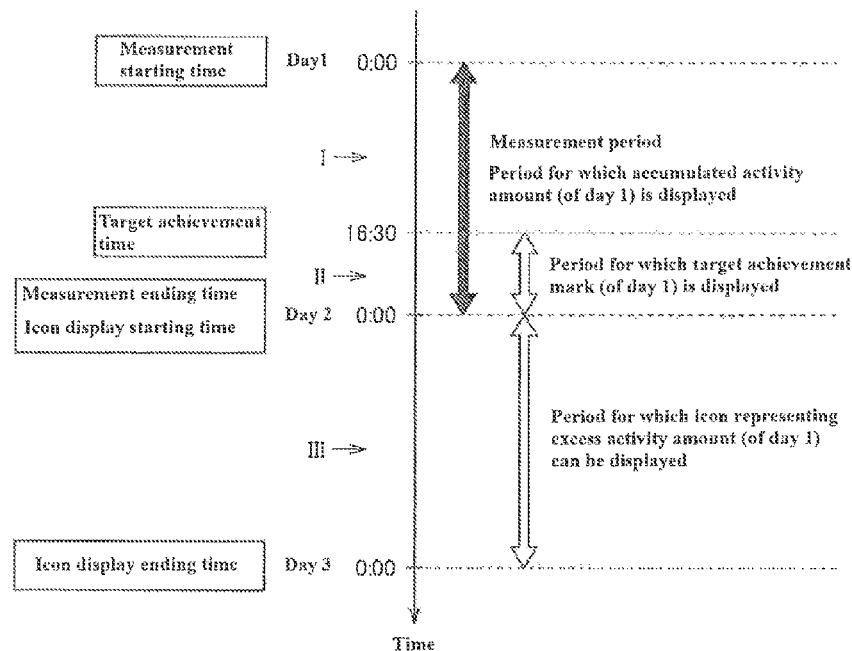
FIG. 2 is a time chart illustrating a display operation of the activity meter illustrated in FIG. 1.
Figure 3:
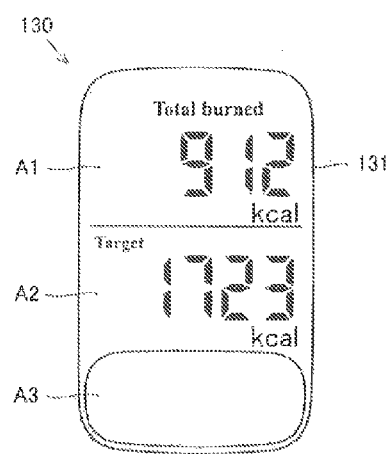
FIG. 3 is a diagram illustrating a display example of a display unit of the activity meter illustrated in FIG. 1 during a measurement period (before achievement of a target).
Figure 4:
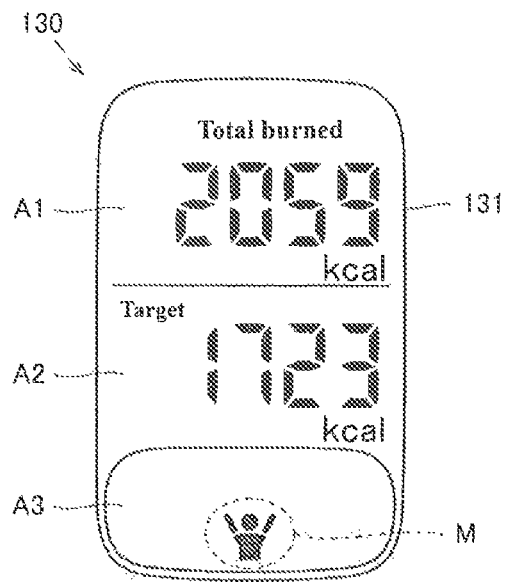
FIG. 4 is a diagram illustrating a display example of the display unit of the activity meter illustrated in FIG. 1 during the measurement period (after achievement of the target).
Figure 5:
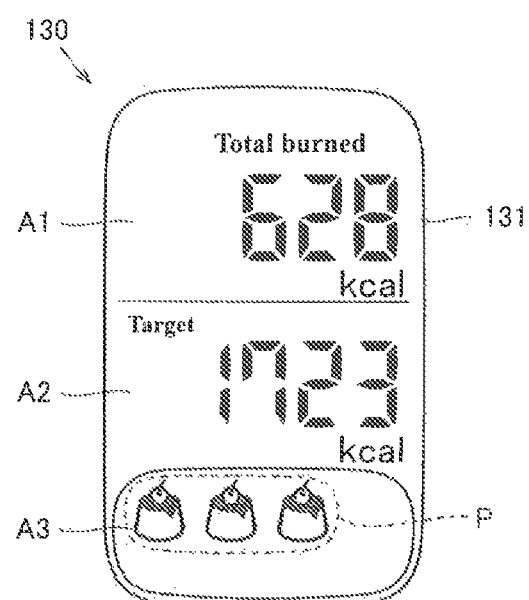
FIG. 5 is a diagram illustrating a display example of the display unit of the activity meter illustrated in FIG. 1 after the measurement period has elapsed.

FIG. 2 is a time chart illustrating a display operation of the activity meter illustrated in FIG. 1. FIGS. 3 to 5 are diagrams illustrating display examples of the display unit of the activity meter illustrated in FIG. 1, where FIG. 3 illustrates a display example during a measurement period (before achievement of a target), FIG. 4 illustrates a display example during the measurement period (after achievement of the target), and FIG. 5 illustrates a display example after the measurement period has elapsed. Next, referring to FIGS. 2 to 5, a display operation of the display unit 130 of the activity meter 1A according to this preferred embodiment and the display examples will be described in detail in accordance with the passage of time. Note that in the time chart illustrated in FIG. 2, to facilitate understanding, only a time period corresponding to day 1 of the period for which the above-described measurement of the amount of activity should be continuously performed is extracted and illustrated as the measurement period. Also, various types of display periods are extracted and illustrated only with respect to day 1 and day 2 for which the measurement result of day 1 is displayed.

As illustrated in FIG. 2, in the activity meter 1A of this preferred embodiment, the measurement of the amount of activity is started at 0:00 on day 1, which is the measurement starting time, and the measurement of the amount of activity is ended at 0:00 on day 2, which is the measurement ending time.

With respect to the measurement result regarding the amount of activity of day 1, which is the measurement period, the accumulated amount of activity is numerically displayed on the display unit 130 at all times on day 1, and the excess amount of activity can be displayed on the display unit 130 on day 2 by icon-based representation. Here, although the icon-based representation on day 2 can be displayed at all times on day 2 after the lapse of the measurement period on day 1, it is actually displayed after the above-described display operation unit 141 is operated, and afterward displayed at all times until the icon display ending time (0:00 on day 3). Note that if the accumulated amount of activity reaches the target amount of activity at a point in time in the middle of day 1, display on the display unit 130 is partially changed at or after the target achievement time (16:30 on day 1 in the example illustrated in FIG. 2) at which the target is achieved.

More specifically, as illustrated in FIG. 3, during a time period on day 1, which is the measurement period, and until the target achievement time (e.g., at a point in time indicated by reference symbol I in FIG. 2), the accumulated amount of activity at that point in time on day 1 is numerically displayed in an upper display region A1 of a display region 131 of the display unit 130, and the target amount of activity of day 1 is numerically displayed in a middle display region A2.

This enables the user to understand the relationship between the target amount of activity and the accumulated amount of activity at that point in time as numerical values. Note that at this point in time, the user's concern is mainly whether the target of the day was achieved or how much more activities the user needs to perform to achieve the target when compared with the activities the user previously performed, and so display of the measurement result by the above-described simple numerical representation will suffice.

As illustrated in FIG. 4, during a time period on day 1, which is the measurement period, and after the target achievement time (e.g., at a point in time indicated by reference symbol II in FIG. 2), the accumulated amount of activity at that point in time on day 1 is numerically displayed in the upper display region A1 of the display region 131 of the display unit 130, the target amount of activity of day 1 is numerically displayed in the middle display region A2, and a target achievement mark M (as illustrated in FIG. 4, for example, a mark of a design that shows a person with the arms up in the air) that is suggestive of the fact that the accumulated amount of activity has already reached the target amount of activity at that point in time on day 1 is displayed in a lower display region A3 by mark-based representation.

This makes it possible for the user to understand the relationship between the target amount of activity and the accumulated amount of activity at that point in time as numerical values and also to understand the achievement of the target by mark-based representation with the target achievement mark M. Note that at this point in time, the user's concern is mainly whether the target of the day was achieved or how much activities the user performed after the achievement of the target in excess of the activities the user performed before the achievement of the target, and so the display of the measurement result by the above-described simple numerical representation and mark-based representation will suffice.

As illustrated in FIG. 5, on day 2 (e.g., at a point in time indicated by reference symbol III in FIG. 2) after the end of the measurement period, the accumulated amount of activity at that point in time on day 2 is numerically displayed in the upper display region A1 of the display region 131 of the display unit 130, the target amount of activity of day 2 is numerically displayed in the middle display region A2, and the excess amount of activity of day 1 is displayed in the lower display region A3 by icon-based representation with icons P.

Here, the icons P that represent the excess amount of activity displayed in the lower display region A3 correspond to an example of display of the measurement result using the above-described converted value, and more specifically, each of the icons P is of a design that shows a predetermined food (e.g., a pudding). To display the icons P, the burned calories corresponding to the excess amount of activity of day 1 is divided by a standard calorie count of that predetermined food (in the case of the puddings, 100 kcal per pudding, for example) to obtain the converted value, and as many icons P as a number corresponding to the converted value are displayed. Note that the icons P may be displayed in units of one icon P by discarding all numbers to the right of the decimal point of the calculated converted value, or may be displayed in units of one-half or in units of one-third by performing similar processing.

This makes it possible for the user to understand the excess amount of activity of day 1, which is the day before, by the number of icons P of a design that shows a food and to intuitively and specifically understand how hard the user is working on a diet. That is to say, for example, in the case where a display example such as that illustrated in FIG. 5 is displayed on the display unit 130, the user can intuitively and specifically understand to what extent he/she is working hard on the diet such that the user thinks, "Yesterday, I got as much exercise in excess of the target amount of activity as calories I can reduce by giving up eating food corresponding to three puddings", and can be motivated to work even harder on the diet.

Here, in the case where a display operation as described above is adopted, the excess amount of activity of day 1, which is the measurement period, is not displayed by icon-based representation until day 2, which is the day that comes directly after the measurement period, and this also can provide an effect of preventing induction of excessive calorie intake after the achievement of the target on day 1. That is to say, in many cases, the user usually confirms the day's accumulated amount of activity during a night time period around or after dinner. At this time, if the day's measurement result until that point in time is displayed using an icon as described above, if the excess amount of activity is sufficient, the user will be likely to have an optimistic view that it may not matter even if he/she eats a late-night meal or the like within a range that can be cancelled out by this excess amount of activity. This may result in a problem in that the diet is not promoted. However, the adoption of a display operation as described above will solve this problem and promote the diet even further.

Note that, as described above, the activity meter 1A of this preferred embodiment is preferably configured so that if the user performs a predetermined operation, a measurement result with respect to each day, which is a unit time period, stored in the storage unit 160 can be displayed on the display unit 130. At this time, it is preferable that the display operation control unit 123 controls the display operation of the display unit 130 such that the accumulated amount of activity of a selected day and an icon P representing the excess amount of activity of the day directly before the selected day are simultaneously displayed on the display unit 130.

With this configuration, when confirming the past measurement results, it is possible to visually confirm the accumulated amount of activity of the selected day and the excess amount of activity of the day that is directly before the selected day as a matched pair at the same time. Thus, based on the excess amount of activity of the day before, it is possible to understand at first glance how hard the user worked on the diet on that selected day without offsetting the excess amount of activity or the extent to which the excess amount of activity was offset because he/she did not work very hard on the diet. This not only facilitates confirmation of the result, but also contributes to promotion of the diet.

Figure 6:
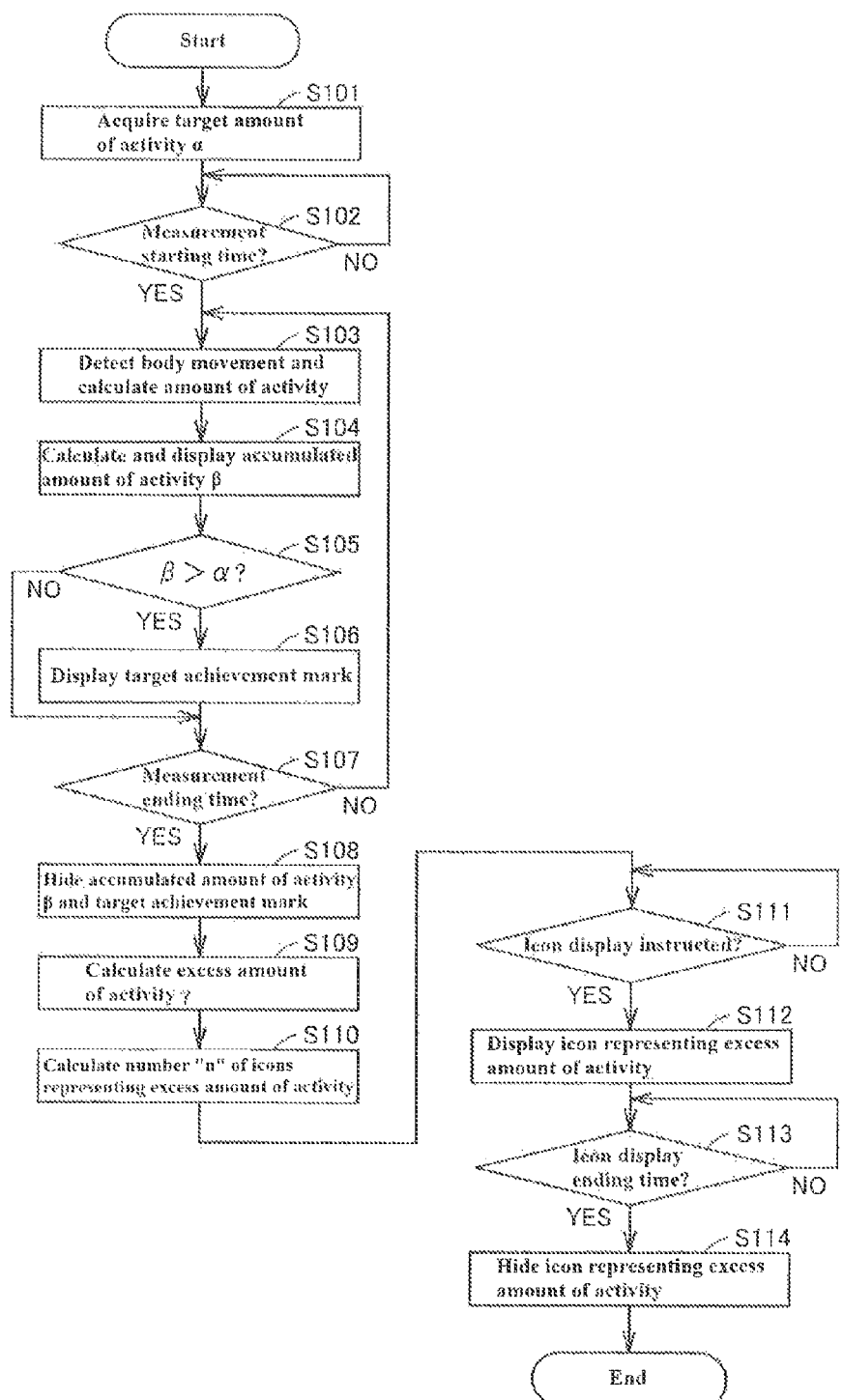
FIG. 6 is a flowchart illustrating operations of a control unit of the activity meter illustrated in FIG. 1.

FIG. 6 is a flow chart illustrating operations of the control unit of the activity meter illustrated in FIG. 1. Next, referring to FIG. 6, the flow of the operations of the control unit 120 of the activity meter 1A according to this preferred embodiment to realize a display operation as described above will be described. Note that, to facilitate understanding, the flow chart illustrated in FIG. 6 extracts and indicates only the operations of the control unit 120 related to measurement on day 1 and the operations of the control unit 120 related to display of the measurement result on day 1 in the case where only a time period corresponding to day 1 is extracted as the measurement period out of a period for which the above-described measurement of the amount of activity should be continuously performed.

As illustrated in FIG. 6, first, the control unit 120 acquires a target amount of activity $\alpha$ (step S101). Specifically, the control unit 120 reads out the target amount of activity $\alpha$ that is stored in the storage unit 160 in advance, thus acquiring the target amount of activity $\alpha$.

Then, the control unit 120 judges whether or not it is the measurement starting time (i.e., 0:00 on day 1) (step S102). Specifically, the control unit 120 judges whether or not the current time acquired by the timing unit 121 has reached the above-described measurement starting time. If it is judged that the current time has not yet reached the measurement starting time (if it is judged NO in step S102), the control unit 120 waits until the measurement starting time is reached.

If it is judged that the current time has reached the measurement starting time (if it is judged YES in step S102), the control unit 120 detects body movement and calculates the amount of activity (step S103). Specifically, the arithmetic processing unit 122 of the control unit 120 calculates the amount of activity based on the body movement detected by the body movement detecting unit 110. Although a description of a specific method for calculating the amount of activity is not given here, it is possible to calculate the amount of activity by, for example, associating information regarding time that is measured by the timing unit with information regarding the body movement that is detected by the body movement detecting unit 110. That is to say, the use of a predetermined algorithm enables clear determination of the type (walking, housework, desk work, jogging, or the like) of the activity of the user based on information on how often and in what magnitude body movement has been detected, in what direction body movement has been detected, and so on, and the amount of activity can be calculated based on the result of this determination.

Then, the control unit 120 calculates and displays an accumulated amount of activity β (step S104). Specifically, the accumulated activity amount calculation unit 122b calculates the accumulated amount of activity β from the above-described measurement starting time based on the amount of activity calculated in step S102 above, and the display operation control unit 123 instructs the display unit 130 to display this calculation result. Thus, the accumulated amount of activity β is numerically displayed on the display unit 130.

Then, the control unit 120 judges whether or not the accumulated amount of activity β is larger than the target amount of activity α (step S105). If the control unit 120 judges that the accumulated amount of activity β is larger than the target amount of activity α (if it is judged YES in step S105), the display operation control unit 123 instructs the display unit 130 to display the target achievement mark M on the display unit 130 (step S106). Thus, the target achievement mark M is displayed on the display unit 130.

If the control unit 120 judges that the accumulated amount of activity β is smaller than or equal to the target amount of activity α (if it is judged NO in step S105), and if the control unit 120 judges that the accumulated amount of activity β is larger than the target amount of activity α (if it is judged YES in step S105) and after the target achievement mark M is displayed on the display unit 130, the control unit 120 judges whether or not it is the measurement ending time (i.e., 0:00 on day 2) (step S107). Specifically, the control unit 120 judges whether or not the current time acquired by the timing unit 121 has reached the above-described measurement ending time. If it is judged that the current time has not yet reached the measurement ending time (if it is judged NO in step S107), the control unit 120 repeats processing of steps S103 to S106 until the measurement ending time is reached. At this time, if the target achievement mark M has already been displayed, the control unit 120 maintains this display state in step S106.

If it is judged that the current time has reached the measurement ending time (if it is judged YES in step S107), the control unit 120 hides both of the numerical representation of the accumulated amount of activity β and the mark-based representation of the target achievement mark M (step S108). Specifically, the display operation control unit 123 outputs to the display unit 130 an instruction to hide both of the numerical representation of the accumulated amount of activity β and the mark-based representation of the target achievement mark M, and in response to this instruction, the display unit 130 cancels the display of these representations. At this time, if the target achievement mark M is not displayed, the control unit 120 maintains this non-display state.

Then, the control unit 120 calculates an excess amount of activity γ (step S109). Specifically, the excess activity amount calculation unit 122c performs arithmetic processing of subtracting the target amount of activity α from the accumulated amount of activity β, thus calculating the excess amount of activity γ.

Then, the control unit 120 calculates the number "n" of icons P that represents the excess amount of activity (step S110). Specifically, the converted value calculation unit 122d performs arithmetic processing of dividing the excess amount of activity γ by a unit calorie count corresponding to a standard calorie count of a predetermined food, thus calculating the above-described converted value, and calculates the number "n" of icons P, which represents the converted value of activity, based on the calculated converted value. After that, there is a shift to the time period for which the excess amount of activity can be displayed by icon-based representation, which is illustrated in FIG. 2.

Then, the control unit 120 judges whether or not an instruction to perform icon display has been issued (step S111). Specifically, the control unit 120 judges whether or not the user has operated the display operation unit 141, and if it is determined that the display operation unit 141 has not been operated (if it is judged NO in step S111), the control unit 120 waits until the display operation unit 141 is operated.

If it is judged that the display operation unit 141 has been operated (if it is judged YES in step S111), the control unit 120 displays an icon P that represents the excess amount of activity (step S112). Specifically, based on the number "n" of icons P calculated in step S110 above, the display operation control unit 123 instructs the display unit 130 to display as many icons P as that number "n" of icons P. Thus, the excess amount of activity is displayed on the display unit 130 by icon-based representation.

Then, the control unit 120 judges whether or not it is the icon display ending time (i.e., 0:00 on day 2) (step S113). Specifically, the control unit 120 judges whether or not the current time acquired by the timing unit 121 has reached the above-described icon display ending time. If it is judged that the current time has not yet reached the icon display ending time (if it is judged NO in step S113), the control unit 120 waits until the icon display ending time is reached.

If it is judged that the current time has reached the icon display ending time (if it is judged YES in step S113), the control unit 120 hides the icons P representing the excess amount of activity (step S114). Specifically, the display operation control unit 123 outputs an instruction to hide the icons P to the display unit 130, and in response to this instruction, the display unit 130 cancels the display of the icons P.

When the control unit 120 operates in accordance with the flow of operations as described above, the flow of the display operation in accordance with the time chart as illustrated in FIG. 2 is realized.

As described above, with the activity meter 1A according to this preferred embodiment, it is possible to provide an activity meter that enables the user to more intuitively and specifically understand how hard he/she is working on the diet. Therefore, the use of the activity meter 1A provides a strong motivation for sticking to the diet and promotes the diet.

Preferred Embodiment 2

Figure 7:
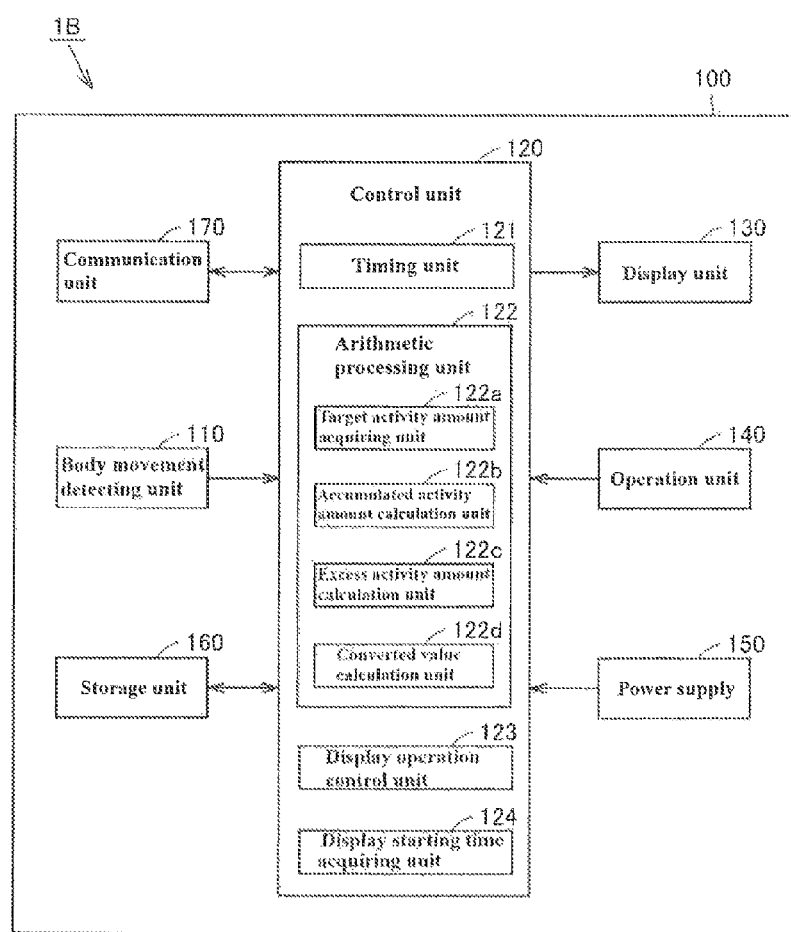
FIG. 7 is a diagram illustrating the configuration of functional blocks of an activity meter according to Preferred Embodiment 2 of the present invention.
Figure 8:
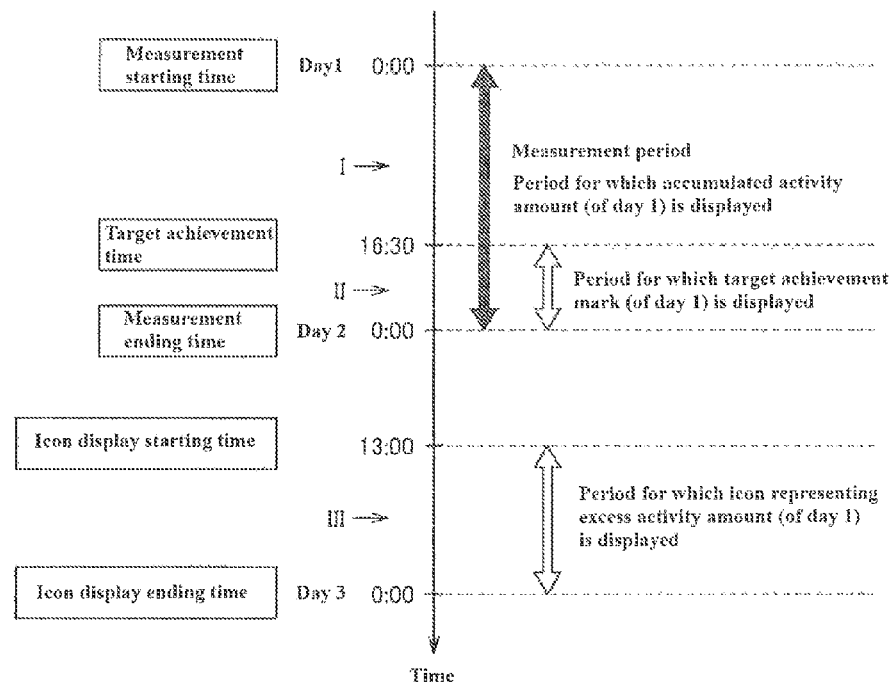
FIG. 8 is a time chart illustrating a display operation of the activity meter illustrated in FIG. 7.
Figure 9:
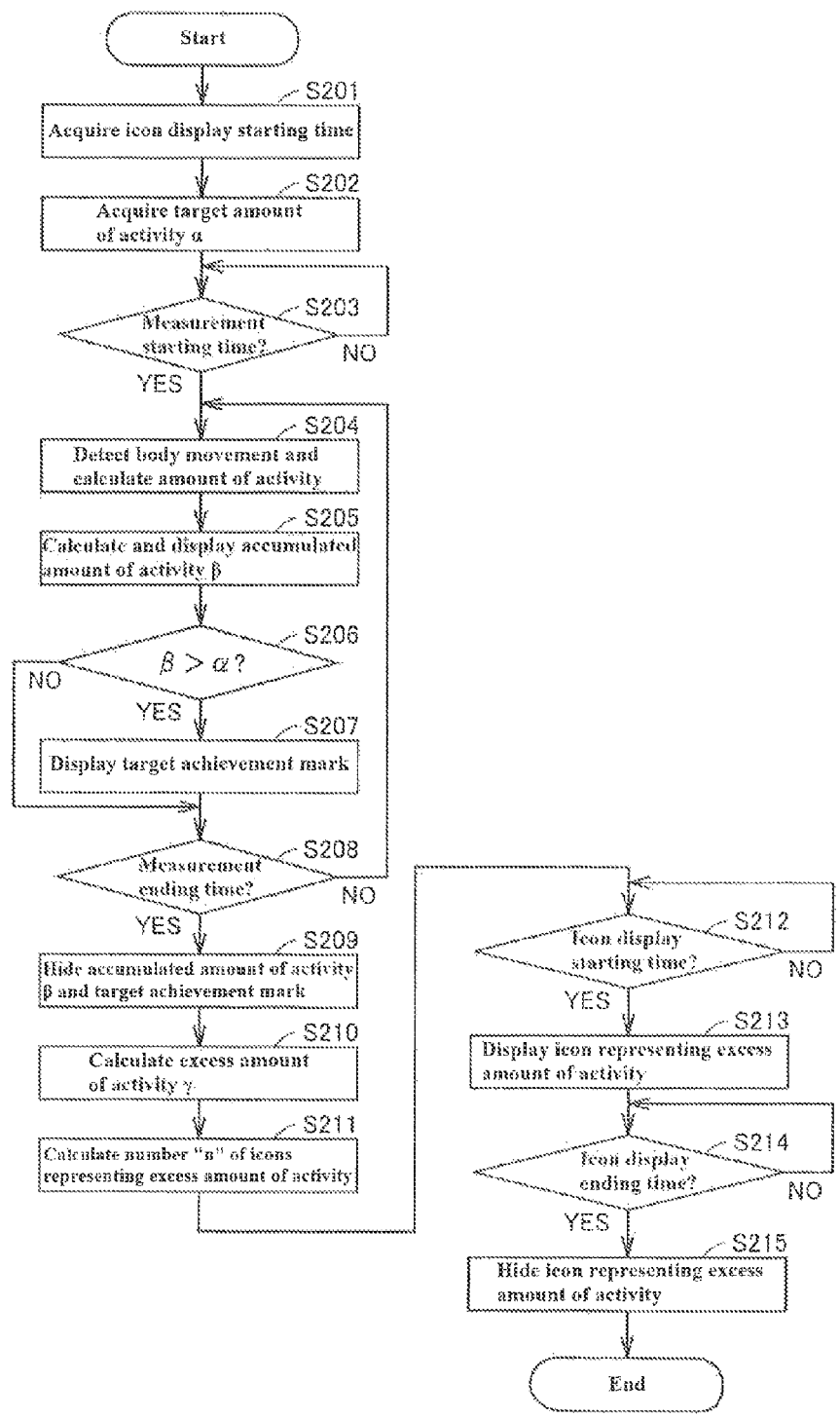
FIG. 9 is a flowchart illustrating operations of a control unit of the activity meter illustrated in FIG. 7.

FIG. 7 is a diagram illustrating the configuration of functional blocks of an activity meter according to Preferred Embodiment 2 of the present invention. FIG. 8 is a time chart illustrating a display operation of the activity meter illustrated in FIG. 7, and FIG. 9 is a flow chart illustrating operations of a control unit of the activity meter illustrated in FIG. 7. Hereinafter, an activity meter 1B of this preferred embodiment will be described with reference to FIGS. 7 to 9. Note that, to facilitate understanding, FIGS. 8 and 9 illustrate the time chart and the flow chart, respectively, under the same conditions as those of FIGS. 2 and 6.

As illustrated in FIG. 7, the activity meter 1B of this preferred embodiment is different from the activity meter 1A of Preferred Embodiment 1 in that the control unit 120 further includes a display starting time acquiring unit 124 in addition to the timing unit 121, the arithmetic processing unit 122, and the display operation control unit 123. The display starting time acquiring unit 124 acquires a starting time at which icon display on the display unit 130 should be enabled. At the activation of the activity meter 1B, this unit acquires a predetermined icon display starting time or acquires any desired icon display starting time that is selected by the user in advance during usage of the activity meter 1B. Note that cases where a configuration is used in which the user selects an icon display starting time in advance, the operation unit 140 can be provided with an icon display starting time input function.

Moreover, unlike the activity meter 1A of Preferred Embodiment 1 described above, the activity meter 1B of this preferred embodiment does not include the display operation unit 141 that causes the display unit 130 to perform a specific display operation (i.e., operation unit that causes icon display to be executed only after the display operation unit 141 is operated during the period for which the excess amount of activity can be displayed by icon-based representation).

As illustrated in FIG. 8, in the activity meter 1B of this preferred embodiment, with respect to the measurement result regarding the amount of activity of day 1, which is the measurement period, the accumulated amount of activity is numerically displayed on the display unit 130 at all times on day 1, and the excess amount of activity is displayed on the display unit 130 by icon-based representation at all times during an icon display period for the excess amount of activity on day 2 (in the example illustrated in FIG. 8, a time period beginning from 13:00 on day 2, which is the icon display starting time, to 0:00 on day 3, which is icon display ending time). Moreover, in the activity meter 1B of this preferred embodiment, no icon that represents the amount of activity of day 1, which is the measurement period, is displayed during a time period between the measurement ending time (0:00 on day 2) and the above-described icon display starting time.

Thus, during the icon display period for the excess amount of activity on day 2, the user can understand the excess amount of activity of day 1, which is the day before, by confirming the icon display. On the other hand, during a time period until the icon display starting time on day 2, the user cannot confirm the excess amount of activity of day 1, which is the day before.

Accordingly, setting the icon display starting time to an appropriate time makes it possible for the user to intuitively and specifically understand how hard he/she is working on the diet during the icon display period for the excess amount of activity on day 2. In addition, during the time period until the icon display starting time on day 2, the user can be prevented from feeling the temptation to think that it may not matter even if he/she eats a meal within a range that can be cancelled out by the excess amount of activity.

For example, in cases where the user's bedtime is later than 0:00, it is assumed that if the user can confirm the icon display representing the excess amount of activity of day 1, which is the day before, during a time period from 0:00 on day 2 to bedtime, the user will feel the temptation to think that it may not matter even if he/she eats a late-night meal or the like within a range that can be cancelled out by the excess amount of activity. In that case, however, setting the icon display starting time to a time that is later than bedtime will solve this problem and promote the diet.

Moreover, in the case of a user who tends to overeat at breakfast and at lunch, it is assumed that if the user can confirm the icon display representing the excess amount of activity of day 1, which is the day before, during a time period from 0:00 on day 2 to lunchtime, the user will feel the temptation to think that it may not matter even if he/she eats breakfast and lunch too much within a range that can be cancelled out by that excess amount of activity. In that case, however, setting the icon display starting time to a time that is later than lunchtime will solve this problem and promote the diet.

Next, referring to FIG. 9, a description will be given of the flow of operations of the control unit 120 of the activity meter 1B according to this preferred embodiment to realize a display operation such as that described above.

As illustrated in FIG. 9, first, the control unit 120 acquires the icon display starting time (step S201). Specifically, the display starting time acquiring unit 124 of the control unit 120 reads out the icon display starting time that is stored in the storage unit 160 in advance, thus acquiring the icon display starting time.

After that, in steps S202 to S211, the control unit 120 performs the same processing as in steps S101 to S110 described in Preferred Embodiment 1 above. Details of this processing overlap with the description of Preferred Embodiment 1 and thus will not be repeated here.

After the processing in step S211 is completed, the control unit 120 judges whether or not it is the icon display starting time (step S212). Specifically, the control unit 120 judges whether or not the current time acquired by the timing unit 121 has reached the icon display starting time. If it is judged that the current time has not yet reached the icon display starting time (if it is judged NO in step S212), the control unit 120 waits until the icon display starting time is reached.

If it is judged that the current time has reached the icon display starting time (if it is judged YES in step S212), the control unit 120 displays an icon P that represents the excess amount of activity (step S213). Specifically, based on the number "n" of icons P calculated in step S211 above, the display operation control unit 123 instructs the display unit 130 to display as many icons P as the number "n" of icons P. Thus, the excess amount of activity is displayed on the display unit 130 by icon-based representation.

After that, in steps S214 and S215, the control unit 120 performs the same processing as in steps S113 and S114 described in Preferred Embodiment 1 above. Details of this processing overlap with the description of Preferred Embodiment 1 and thus will not be repeated here.

When the control unit 120 operates in accordance with the flow of the operations as described above, the flow of a display operation in accordance with the time chart as illustrated in FIG. 8 is realized.

As described above, with the activity meter 1B of this preferred embodiment, it is possible to provide an activity meter that enables the user to more intuitively and specifically understand how hard he/she is working on the diet, while preventing the user from feeling the temptation to think that it may not matter even if he/she eats a meal within a range that can be cancelled out by the excess amount of activity. Accordingly, the use of the activity meter 1B will promote the diet even further.

Preferred Embodiment 3

Figure 10:
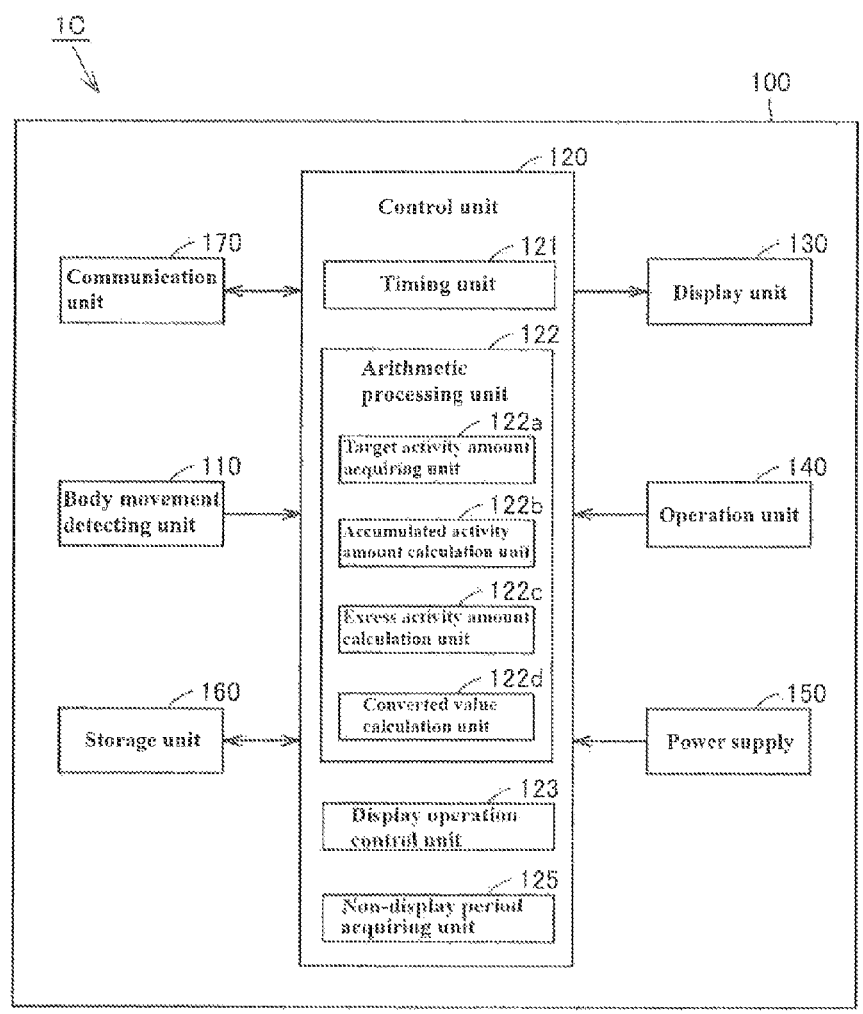
FIG. 10 is a diagram illustrating the configuration of functional blocks of an activity meter according to Preferred Embodiment 3 of the present invention.
Figure 11:
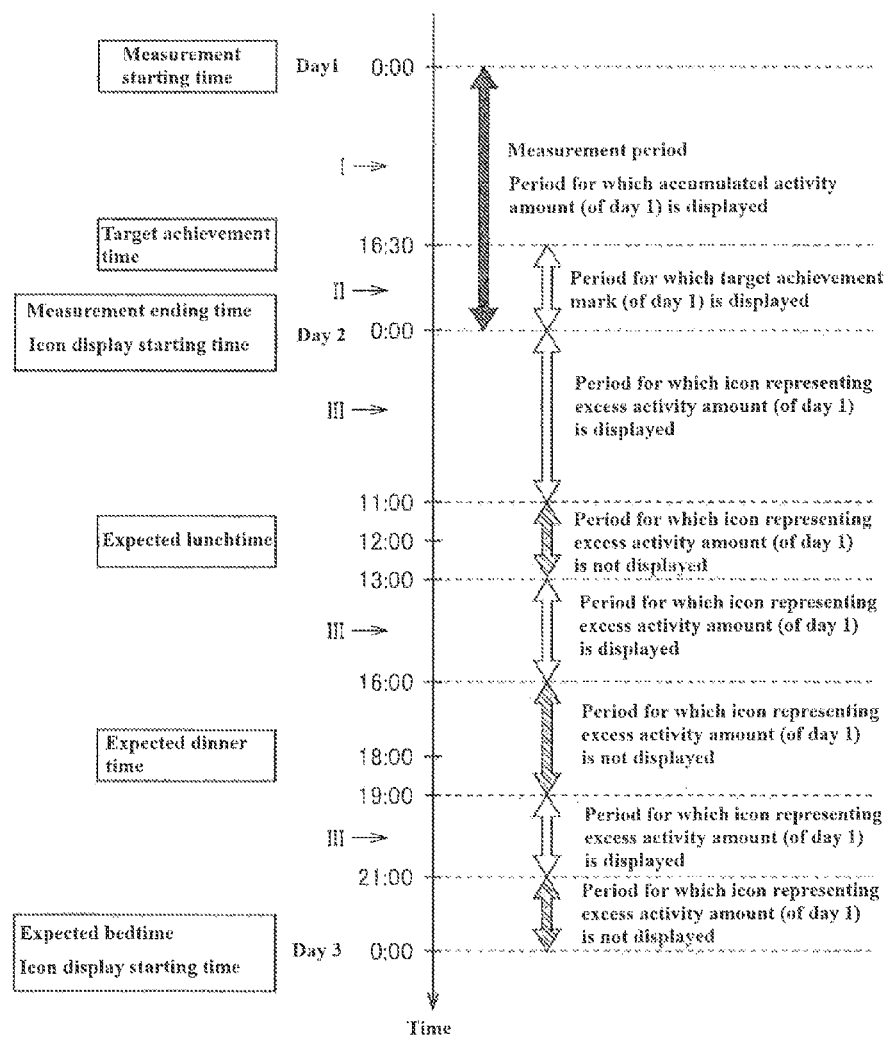
FIG. 11 is a time chart illustrating a display operation of the activity meter illustrated in FIG. 10.
Figure 12:
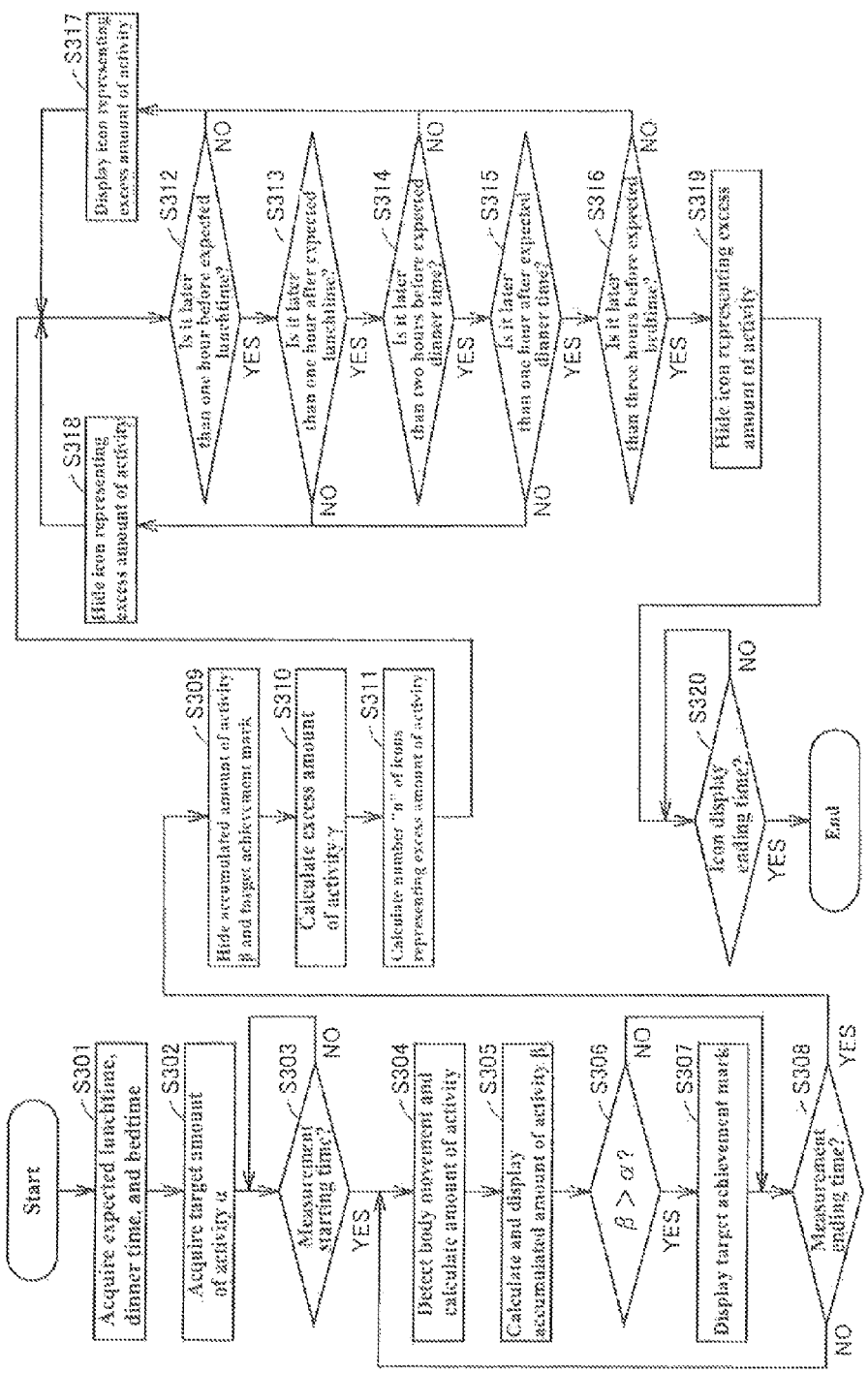
FIG. 12 is a flow chart illustrating operations of a control unit of the activity meter illustrated in FIG. 10.

FIG. 10 is a diagram illustrating the configuration of functional blocks of an activity meter according to Preferred Embodiment 3 of the present invention. FIG. 11 is a time chart illustrating a display operation of the activity meter illustrated in FIG. 10, and FIG. 12 is a flow chart illustrating operations of the control unit of the activity meter illustrated in FIG. 10. Hereinafter, an activity meter 1C of this preferred embodiment will be described with reference to FIGS. 10 to 12. Note that, to facilitate understanding, FIGS. 11 and 12 illustrate the time chart and the flow chart, respectively, under the same conditions as in FIGS. 2 and 6 described above.

As illustrated in FIG. 10, the activity meter 1C of this preferred embodiment is different from the activity meter 1A of Preferred Embodiment 1 above in that the control unit 120 further includes a non-display period acquiring unit 125 in addition to the timing unit 121, the arithmetic processing unit 122, and the display operation control unit 123. The non-display period acquiring unit 125 acquires a non-display period for which icon display should not be displayed on the display unit 130. At the activation of the activity meter 1C, the non-display period acquiring unit 125 acquires a predetermined non-display period or acquires any desired non-display period that is selected by the user in advance during usage of the activity meter 1C.

Here, in the case where a configuration is used in which the user selects an icon non-display period in advance, the operation unit 140 can be provided with a time input function that determines the icon non-display period. In that case, a configuration may be used in which the starting time and the ending time of that non-display period are directly and independently input, or a configuration may be used in which, for example, when an expected lunchtime, an expected dinner time, and an expected bedtime are input, a specific time period around each of the expected times input is automatically set as the non-display period. Note that it is supposed that the activity meter 1C of this preferred embodiment is configured so that when an expected lunchtime, an expected dinner time, and an expected bedtime are input, a specific time period around each of the expected times is automatically set as the non-display period.

Moreover, unlike the activity meter 1A of Preferred Embodiment 1 described above, the activity meter 1C of this preferred embodiment does not include the display operation unit 141 that causes the display unit 130 to perform a specific display operation (i.e., operation unit that causes icon display to be executed only after the display operation unit 141 is operated during a period for which the excess amount of activity can be displayed by icon-based representation).

As illustrated in FIG. 10, in the activity meter 1C of this preferred embodiment, with respect to the measurement result regarding the amount of activity of day 1, which is the measurement period, the accumulated amount of activity is numerically displayed on the display unit 130 at all times on day 1, and the excess amount of activity is displayed by icon-based representation on the display unit 130 at all times during time periods on day 2 excluding icon non-display periods with respect to the excess amount of activity (in the example illustrated in FIG. 10, a time period from one hour before to one hour after 12:00, which is the expected lunchtime, on day 2 (i.e., a time period from 11:00 to 13:00 on day 2), a time period from two hours before and one hour after 18:00, which is the expected dinner time, on day 2 (i.e., a time period from 16:00 to 19:00 on day 2), and a time period of three hours before 0:00, which is the expected bedtime, on day 3 (i.e., a time period from 21:00 on day 2 to 0:00 on day 3)), or in other words, during a time period from 0:00 to 11:00 on day 2, a time period from 13:00 to 16:00 on day 2, and a time period from 19:00 to 21:00 on day 2. Moreover, in the activity meter 1C of this preferred embodiment, no icon that represents the amount of activity of day 1, which is the measurement period, is displayed during the above-described non-display periods.

Thus, during an icon display period on day 2 with respect to the excess amount of activity, the user can understand the excess amount of activity of day 1, which is the day before, by confirming the icon display. On the other hand, during an icon non-display period on day 2 with respect to the excess amount of activity, the user cannot confirm the excess amount of activity of day 1, which is the day before.

Accordingly, setting the icon non-display period to an appropriate time period makes it possible for the user to intuitively and specifically understand how hard he/she is working on the diet during the icon display period on day 2 with respect to the excess amount of activity, and also makes it possible for the user to be prevented from feeling the temptation to think that it may not matter even if he/she eats a meal within a range that can be cancelled out by the excess amount of activity during the icon non-display period on day 2.

For example, in the case of a user who tends to eat too much at lunch and at dinner, it is assumed that if the user can confirm the icon display that represents the excess amount of activity of day 1, which is the day before, during time periods around lunchtime and dinner time, the user will feel the temptation to think that it may not matter even if he/she eats lunch and dinner too much within a range that can be cancelled out by that excess amount of activity. In that case, however, setting the icon non-display period so as to contain time periods around lunchtime and dinner time will solve this problem and promote the diet.

Moreover, in the case of a user who tends to eat a late-night meal before going to bed, it is assumed that if the user can confirm the icon display that represents the excess amount of activity of day 1, which is the day before, during a time period before bedtime, the user will feel the temptation to think that it may not matter even if he/she eats a late-night meal within a range that can be cancelled out by that excess amount of activity. In that case, however, setting the icon non-display period so as to contain a time period before bedtime will solve this problem and promote the diet.

Next, referring to FIG. 12, a description will be given of the flow of operations of the control unit 120 of the activity meter 1C according to this preferred embodiment for realizing a display operation as described above.

As illustrated in FIG. 12, first, the control unit 120 acquires an icon non-display period (step S301). Specifically, the non-display period acquiring unit 125 of the control unit 120 reads out an expected lunchtime, an expected dinner time, and an expected bedtime that are stored in the storage unit 160 in advance, thus acquiring icon non-display periods.

After that, in steps S302 to S311, the control unit 120 performs the same processing as in steps S101 to S110 described in Preferred embodiment 1 above. Details of this processing overlap with the description of Preferred embodiment 1 and thus will not be repeated here.

After the processing in step S311 is completed, the control unit 120 judges whether or not it is during any of the non-display periods by performing a series of processing steps in steps S312 to S316. Specifically, in step S312, the control unit 120 judges whether or not the current time acquired by the timing unit 121 is later than one hour before the expected lunchtime. In step S313, the control unit 120 judges whether or not the current time acquired by the timing unit 121 is later than one hour after the expected lunchtime. In step S314, the control unit 120 judges whether or not the current time acquired by the timing unit 121 is later than two hours before the expected dinner time. In step S315, the control unit 120 judges whether or not the current time acquired by the timing unit 121 is later than one hour after the expected dinner time. In step S316, the control unit 120 judges whether or not the current time acquired by the timing unit 121 is later than three hours before the expected bedtime.

If it is judged that the current time is not included in any non-display period (if it is judged NO in step S312, S314, or S316), the control unit 120 displays an icon P that represents the excess amount of activity (step S317). Specifically, based on the number "n" of icons P calculated in step S311 above, the display operation control unit 123 instructs the display unit 130 to display as many icons P as the number "n" of icons P. Thus, the excess amount of activity is displayed on the display unit 130 by icon-based representation. At this time, if the icons P have already been displayed, the control unit 120 maintains this display state in step S317.

Alternatively, if it is judged that the current time is included in a non-display period (if it is judged No in step S313 or S315 or if it is judged YES in step S316), the control unit 120 hides any icon P that represents the excess amount of activity (steps S318 and S319). Specifically, the display operation control unit 123 outputs an instruction to hide the icon P to the display unit 130, and in response to this instruction, the display unit 130 cancels the display of the icon P. At this time, if the icon P has already been hidden, the control unit 120 maintains this non-display state in step S318.

After the icon P that represents the excess amount of activity is hidden in step S319, the control unit 120, in step S320, performs the same processing as in step S114 described in Preferred Embodiment 1 above. Details of this processing overlap with the description of Preferred Embodiment 1 and thus will not be repeated here.

When the control unit 120 operates in accordance with the flow of operations as described above, the flow of a display operation in accordance with the time chart as illustrated in FIG. 11 is realized.

As described above, with the activity meter 1C of this preferred embodiment, it is possible to provide an activity meter that enables the user to more intuitively and specifically understand how hard he/she is working on the diet, while preventing the user from feeling the temptation to think that it may not matter even if he/she eats a meal within a range that can be cancelled out by the excess amount of activity. Therefore, the use of the activity meter 1C will promote the diet even further.

Preferred Embodiment 4

Figure 13:
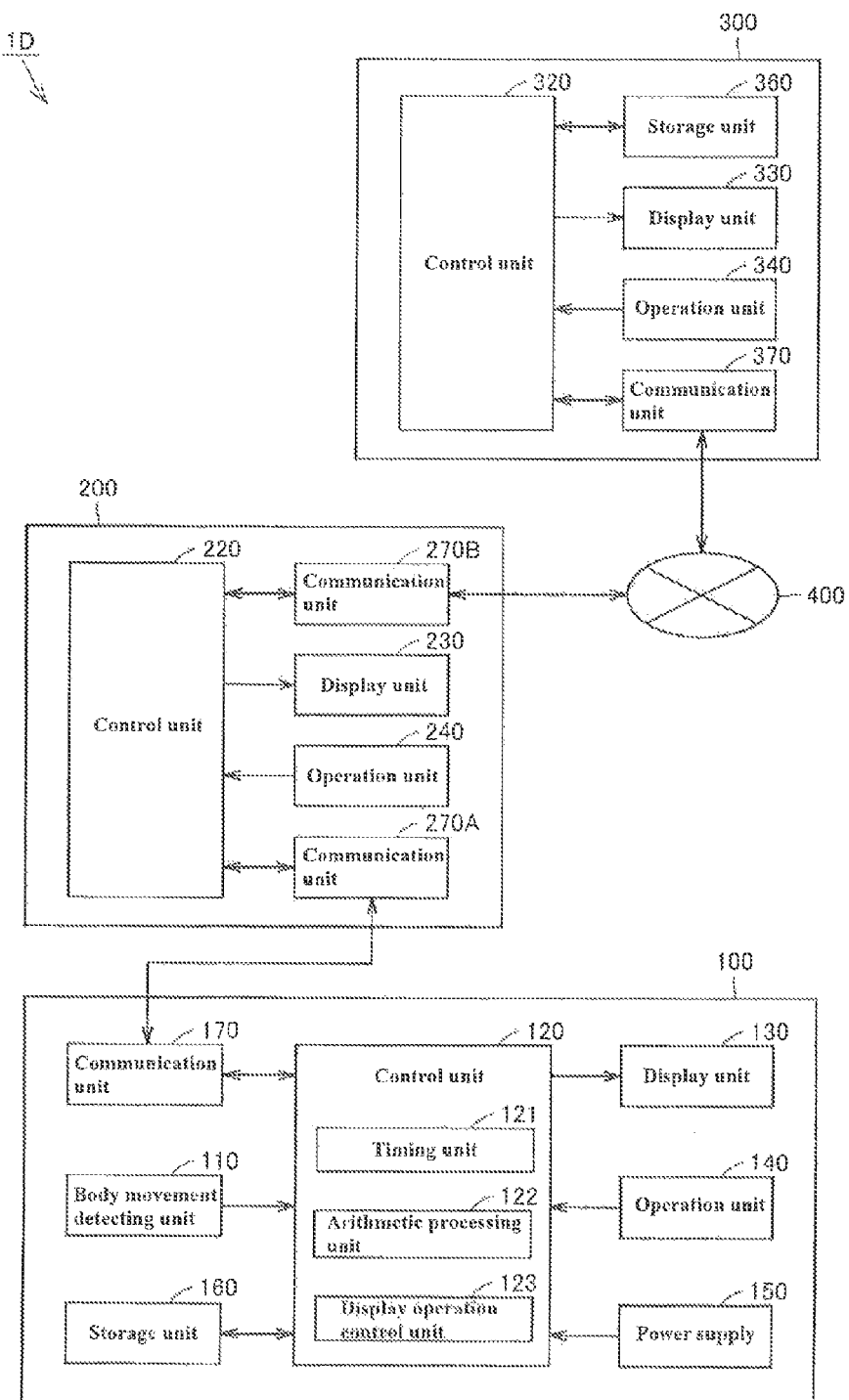
FIG. 13 is a diagram illustrating the configuration of functional blocks of an activity meter according to Preferred Embodiment 4 of the present invention.

FIG. 13 is a diagram illustrating the configuration of functional blocks of an activity meter according to Preferred Embodiment 4 of the present invention. Hereinafter, an activity meter 1D of this preferred embodiment will be described with reference to FIG. 13.

As illustrated in FIG. 13, unlike the above-described activity meter 1A of Preferred Embodiment 1, the activity meter 1D of this preferred embodiment further includes an external terminal 200 and a management terminal 300, which is a second terminal, in addition to the terminal 100, which is a portable first terminal in which the above-described body movement detecting unit 110 is provided. Here, the external terminal 200 is, for example, an information processing apparatus such as a PC, a smartphone, or a PDA, and the management terminal 300 is, for example, a server. The external terminal 200, which is an information processing apparatus, and the management terminal 300, which is a server, are communicably connected to each other via, for example, the Internet 400.

The terminal 100 is the same as the terminal 100 of Preferred Embodiment 1 described above, and mainly includes the body movement detecting unit 110, the control unit 120, the display unit 130, the operation unit 140, the power supply 150, the storage unit 160, and the communication unit 170.

The external terminal 200 mainly includes a control unit 220, a display unit 230, an operation unit 240, and two communication units 270A and 270B serving as a communication device. The communication unit 270A communicates with the communication unit 170 provided in the above-described terminal 100, and is configured by, for example, a communication interface such as a USB to connect to the terminal 100 through wire or FeliCa (registered trademark), Bluetooth (registered trademark), or the like as NFC to perform wireless communication with the terminal 100. On the other hand, the communication unit 270B is configured by an interface such as a wired LAN board, a wireless LAN board, or the like to connect the external terminal 200 to the Internet 400.

The management terminal 300 mainly includes a control unit 320, a display unit 330, an operation unit 340, a storage unit 360, and a communication unit 370 serving as a communication device. The communication unit 370 is configured by an interface such as a wired LAN board, a wireless LAN board, or the like to connect the management terminal 300 to the Internet 400.

Here, the management terminal 300 has, for example, a function of receiving various types of measurement data (including the above-described converted value that represents the excess amount of activity), which are the measurement results measured by the terminal 100, via the external terminal 200 and the Internet 400 and accumulating the measurement data in the storage unit 360. The external terminal 200 has, for example, a function of loading the various types of data, which are the measurement results, stored in the storage unit 360 of the management terminal 300 via the Internet 400 when necessary and displaying a graph, a table, or the like on the display unit 230 using the loaded various types of data, and a function of causing the display unit 230 to display the history of the excess amount of activity, of the loaded various types of data, during a time period for which measurement of the amount of activity, which is the amount of body movement, should be continuously performed by the above-described icon-based representation using the above-described converted value, which represents the excess amount of activity.

In the case where a configuration such as that of the activity meter 1D according to this preferred embodiment described above is used, in a state in which the terminal 100 is not connected to the external terminal 200 or the like, the user can more intuitively and specifically understand how hard he/she is working on the diet by confirming this on the display unit 130 of the terminal 100. Moreover, in a state in which the terminal 100 is connected to the external terminal 200 or the like, the user can understand more detailed measurement results by confirming the display unit 230 of the external terminal 200. Accordingly, the use of the activity meter 1D will promote the diet even further.

Note that in this preferred embodiment, a case where the terminal 100 is configured so as to be connected to not only the external terminal 200 but also to the management terminal 300 via the Internet 400 has been described as an example. However, the terminal 100 may also be configured so as to be connected to only the external terminal 200. In this case, the various types of measurement data (including the above-described converted value that represents the excess amount of activity), which are the measurement results measured by the terminal 100, can be accumulated in the storage unit 260 of the external terminal 200, and the above-described various functions provided in the management terminal 300 can be provided in the external terminal 200.

In Preferred Embodiments 1 to 4 of the present invention above, the description has been given using a case where a configuration in which the display unit of the terminal 100 performs some kind of display at all times is used as an example. However, it is also possible to use a configuration that is provided with a so-called display sleep mode in which if the user operation is not performed for a certain period of time, the display operation of the display unit 130 is automatically switched off, and if a user operation is performed, the display operation of the display unit 130 is resumed. With this configuration, power consumption can be reduced, and so it is possible to provide an activity meter that can be used for a long period of time.

Moreover, in Preferred Embodiments 1 to 4 of the present invention described above, the description has been given using a case where the excess amount of activity preferably is displayed by icon-based representation as an example. However, text-based representation may also be adopted as an example of the measurement result using the converted value, instead of icon-based representation. Here, text-based representation includes a case where the excess amount of activity as illustrated in FIG. 5 is displayed like, for example, "pudding×3". This configuration also makes it possible to more intuitively and specifically understand the excess amount of activity in terms of how hard the user is working on the diet.

Moreover, all of the times, the time periods, the types of food for use in icon-based representation, and the like that have been described in Preferred Embodiment 1 to 4 of the present invention above are merely examples, and changes can be made thereto as appropriate or desired. For example, the starting time and the ending time of the measurement period may also be changed in accordance with the user's life pattern, or a food other than pudding may also be used as the food for use in icon-based representation.

Furthermore, the characteristic configurations that have been described in Preferred Embodiments 1 to 4 of the present invention above can be combined with one another.

In addition, in Preferred Embodiments 1 to 4 of the present invention above, the description has been given using a case where the present invention is applied to an activity meter as an example. However, preferred embodiments of the present invention are also applicable to a pedometer and other devices, for example.

In this manner, the preferred embodiments and variations thereof disclosed herein are to be considered in all respects as illustrative and not restrictive. The technical scope of the present invention is defined by the appended claims, and all changes that fall within the meaning and scope equivalent to those of the claims are intended to be embraced therein.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A body movement amount measuring apparatus that measures an amount of body movement by detecting body movement, the apparatus comprising:
   a display unit that display a measurement result;
   a target body movement amount acquiring unit that acquires a target amount of body movement in a predetermined time period;
   a body movement detecting unit that detects body movement;
   an accumulated body movement amount calculation unit that calculates an accumulated amount of body movement from a beginning of the predetermined time period based on a detection result of the body movement detecting unit;
   an excess body movement amount calculation unit that calculates an excess amount of body movement by which the accumulated amount of body movement exceeds the target amount of body movement by subtracting the target amount of body movement from the accumulated amount of body movement;
   a converted value calculation unit that calculates a converted value representing the excess amount of body movement by dividing burned calories corresponding to the excess amount of body movement by a unit calorie count, where a standard calorie count of a predetermined food item is the unit calorie count; and
   a display operation control unit that is programmed to control a display operation of the display unit such that the display unit displays a measurement result using the converted value; wherein
   the display operation control unit controls the display operation of the display unit so as to enable the display unit to display the accumulated amount of body movement as the measurement result before the predetermined time period elapses and enable the display unit to display, after the predetermined time period elapses, the measurement result using one or more same icons each representing the predetermined food item, the number of icons corresponding to the converted value.

2. The body movement amount measuring apparatus according to claim 1, further comprising:
   a display operation unit that accepts an instruction to cause the display unit to display the measurement result using the converted value; wherein
   the display operation control unit is programmed to cause the display unit to display the measurement result using the converted value only after the predetermined time period elapses and at a point in time when an initial operation of the display operation unit is accepted.

3. The body movement amount measuring apparatus according to claim 2, wherein the predetermined time period is 24 hours.

4. The body movement amount measuring apparatus according to claim 1, further comprising:
   a display starting time acquiring unit that acquires a starting time from which the display unit should be enabled to display the measurement result using the converted value after the predetermined time period elapses; wherein
   the display operation control unit is programmed to enable the display unit to display the measurement result using the converted value at a point in time when the starting time is reached.

5. The body movement amount measuring apparatus according to claim 1, further comprising:
   a non-display period acquiring unit that acquires a non-display period for which the display unit should not display the measurement result using the converted value after the predetermined time period elapses; wherein
   the display operation control unit causes the display unit to be unable to display the measurement result using the converted value during the non-display period.

6. The body movement amount measuring apparatus according to claim 1, wherein the display operation control unit is programmed to control the display operation of the display unit such that, at a point in time when the accumulated amount of body movement reaches the target amount of body movement, the display unit displays a mark of a design that suggests that the accumulated amount of body movement has reached the target amount of body movement.

7. The body movement amount measuring apparatus according to claim 1, wherein the predetermined time period is taken as a unit time period, and a time period for which measurement of the amount of body movement should be continuously performed is covered by repeating the unit time period.

8. The body movement amount measuring apparatus according to claim 7, further comprising:
   a storage unit that stores the measurement result with respect to each unit time period; wherein
   the display operation control unit is programmed to control the display operation of the display unit such that the measurement result with respect to each unit time period stored in the storage unit is read out and displayed on the display unit for each unit time period.

9. The body movement amount measuring apparatus according to claim 8, wherein when causing the display unit to display the measurement result with respect to each unit time period, the display operation control unit is programmed to cause the display unit to simultaneously display an accumulated amount of body movement in a selected unit time period and a measurement result using a converted value that represents an excess amount of body movement in a unit time period that is immediately before the selected unit time period.

10. The body movement amount measuring apparatus according to claim 1, wherein the body movement detecting unit and the display unit are provided in a single portable terminal.

11. The body movement amount measuring apparatus according to claim 1, further comprising:
   a portable first terminal in which the body movement detecting unit is provided; and
   a second terminal that is communicable with the first terminal via a communication device; wherein
   the converted value is stored in a storage unit provided in the second terminal in a cumulative manner.

12. The body movement amount measuring apparatus according to claim 1, wherein the amount of body movement is an amount of activity or a number of steps.

\* \* \* \* \*